United States Patent
Timms et al.

(10) Patent No.: US 11,759,635 B2
(45) Date of Patent: Sep. 19, 2023

(54) PATIENT STIMULATION DEVICE

(71) Applicant: Teesside University, Middlesbrough (GB)

(72) Inventors: Jason Timms, Nottingham (GB); Cormac Ryan, North Yorkshire (GB); Denis Martin, Durham (GB)

(73) Assignee: Teesside University, Middlesbrough (GB)

( * ) Notice: Subject to any disclaimer, the term of this patent is extended or adjusted under 35 U.S.C. 154(b) by 0 days.

(21) Appl. No.: 16/097,323

(22) PCT Filed: Apr. 28, 2017

(86) PCT No.: PCT/GB2017/051217
§ 371 (c)(1),
(2) Date: Oct. 29, 2018

(87) PCT Pub. No.: WO2017/187202
PCT Pub. Date: Nov. 2, 2017

(65) Prior Publication Data
US 2019/0091471 A1    Mar. 28, 2019

(30) Foreign Application Priority Data
Apr. 29, 2016  (GB) ..................... 1607594

(51) Int. Cl.
*A61N 1/36*  (2006.01)
*A61N 1/04*  (2006.01)

(52) U.S. Cl.
CPC ....... *A61N 1/36025* (2013.01); *A61N 1/0476* (2013.01); *A61N 1/36014* (2013.01); *A61N 1/36021* (2013.01)

(58) Field of Classification Search
CPC combination set(s) only.
See application file for complete search history.

(56) References Cited

U.S. PATENT DOCUMENTS 4,541,432 A  *  9/1985  Molina-Negro ... A61N 1/36021
                                                            607/46
10,022,545 B1 *  7/2018  Giuffrida ............. A61B 5/0488
(Continued)

FOREIGN PATENT DOCUMENTS

| JP | 2007502179 A | 2/2007 |
| WO | 0113793 | 3/2001 |
| WO | 03009757 | 2/2003 |

OTHER PUBLICATIONS

International Search Report and Written Opinion for PCT Application No. PCT/GB2017/051217 dated Sep. 27, 2017; Forms PCT/ISA/210 and PCT/ISA/237; 16 pages.
(Continued)

*Primary Examiner* — Scott Luan
(74) *Attorney, Agent, or Firm* — BOND, SCHOENECK & KING, PLLC; Joseph Noto (57) ABSTRACT

A patient stimulation device is provided comprising a plurality of stimulators for selectively applying a stimulus to a patient's body. Each of the plurality of stimulators is locatable in a different position upon a patient's body. A patient input interface is provided for receiving data representative of a perceived stimulus from the patient, and an output is provided for communicating to a patient data representative of an applied stimulus. The device comprises a controller having a training mode, the training mode comprising the controller actuating at least one of the plurality of stimulators to apply a stimulus to the patient's body, subsequently receiving data representative of a perceived stimulus from the patient input interface, and subsequently providing the output with data representative of the applied stimulus for communication to the patient, such that the data representative of the applied stimulus identifies, or allows the identification of, the applied stimulus.

19 Claims, 7 Drawing Sheets

(56) References Cited

U.S. PATENT DOCUMENTS

| | | | |
|---|---|---|---|
| 10,765,859 B2* | 9/2020 | Bouton | A61B 5/251 |
| 2005/0182456 A1* | 8/2005 | Ziobro | A61B 5/0488 |
| | | | 607/48 |
| 2007/0276448 A1 | 11/2007 | Fairbank et al. | |
| 2011/0264002 A1* | 10/2011 | Kolen | A61N 1/36185 |
| | | | 600/554 |
| 2013/0304176 A1 | 11/2013 | Riddle | |
| 2014/0277582 A1* | 9/2014 | Leuthardt | A61F 2/54 |
| | | | 623/25 |

OTHER PUBLICATIONS

JP2019-508305 Office Action (dated Mar. 18, 2021).

* cited by examiner

PATIENT STIMULATION DEVICE

REFERENCE TO RELATED APPLICATION

This application is a U.S. National Phase filing of International Application No. PCT/GB2017/051217, filed Apr. 28, 2017, which relates and claims priority to Great Britain Application Number 1607594.7, filed Apr. 29, 2016, the entirety of each of which are hereby incorporated by reference in their entirety.

FIELD

The present invention relates to a patient stimulation device, and in particular to a patient stimulation device for sensory discrimination training.

BACKGROUND

In the human brain, there is a mental body image or representation of the physical body. Individuals with long standing chronic pain have an altered mental body image of the painful area. For example, the mental body image of the shape, size, or position of the painful area, relative to the rest of the body, becomes distorted. This is sometimes referred to as cortical reorganisation/disruption or cortical remapping. The amount of cortical reorganisation is associated with the amount of pain in some chronic pain conditions such as phantom limb pain (PLP), where patients experience pain from limbs which are no longer there.

Sensory discrimination training attempts to use stimulation to reverse the effects of cortical reorganisation, and thus reduce the pain felt by a patient. Different types of stimulation may be used, including touch or electrical stimulation or vibrations. Cortical reorganisation may reduce a patient's ability to contextualise and discriminate the different components of the electrical stimulation such as the location and/or form of an applied electrical stimulus. Sensory discrimination training typically involves training a patient to recognise the location and/or form of an applied electrical stimulus, and this may require daily stimulation for a prolonged period of time, for example a period of 2-3 weeks. Theoretically, as the patient's ability to recognise the applied electrical stimulation improves, so the cortical reorgisation changes, towards an improved match between the mental body image of the patient and the physical body part.

Conventional sensory discrimination training methods require the presence of a third party to provide such feedback, with the third party typically being a healthcare professional such as a doctor or a nurse. The need for the presence of a doctor or nurse daily for a period of 2-3 weeks can lead to large costs associated with sensory discrimination training, as well as placing a strain on both resources and the time of a healthcare professional. Attempts to train non-health care practitioners, such as the patient's friends and family, to provide this feedback have been unsuccessful.

SUMMARY

There has now been devised a patient stimulation device, a method of applying a stimulus to a patient's body, and a data carrier comprising machine readable instructions for a controller of a patient stimulation device, which overcome or substantially mitigate the aforementioned and/or other disadvantages associated with the prior art.

According to a first aspect of the present invention there is provided a patient stimulation device comprising a plurality of stimulators for selectively applying a stimulus to a patient's body, each of the plurality of stimulators being locatable in a different position upon a patient's body, a patient input interface for receiving data representative of a perceived stimulus from the patient, and an output for communicating to a patient data representative of an applied stimulus, wherein the device comprises a controller having a mode in which the controller:

(a) actuates at least one of the plurality of stimulators to apply a stimulus to the patient's body,
    (b) subsequently receives data representative of a perceived stimulus from the patient input interface, and
    (c) subsequently provides the output with data representative of the applied stimulus for communication to the patient, such that the data representative of the applied stimulus identifies, or allows the identification of, the applied stimulus.

According to a second aspect of the present invention there is provided a method of applying a stimulus to a patient's body using a patient stimulation device, the device comprising a plurality of stimulators for selectively applying a stimulus to a patient's body, each of the plurality of stimulators being locatable in a different position upon a patient's body, a patient input interface for receiving data representative of a perceived stimulus from the patient, an output for communicating to a patient data representative of an applied stimulus, and a controller having a mode in which the controller:

(a) actuates at least one of the plurality of stimulators to apply a stimulus to the patient's body,
    (b) subsequently receives data representative of a perceived stimulus from the patient input interface, and
    (c) subsequently provides the output with data representative of the applied stimulus for communication to the patient, such that the data representative of the applied stimulus identifies, or allows the identification of, the applied stimulus.

According to a third aspect of the present invention there is provided a data carrier comprising machine readable instructions for a controller of a patient stimulation device, the device comprising a plurality of stimulators for selectively applying a stimulus to a patient's body, each of the plurality of stimulators being locatable in a different position upon a patient's body, a patient input interface for receiving data representative of a perceived stimulus from the patient, an output for communicating to a patient data representative of an applied stimulus, and a controller having a mode in which the instructions cause operation of the controller to:

(a) actuate at least one of the plurality of stimulators to apply a stimulus to the patient's body,
    (b) subsequently receive data representative of a perceived stimulus from the patient input interface, and
    (c) subsequently provide the output with data representative of the applied stimulus for communication to the patient, such that the data representative of the applied stimulus identifies, or allows the identification of, the applied stimulus.

The first, second and third aspects of the present invention may be advantageous principally as the device comprises a controller having a mode in which the controller actuates at least one of the plurality of stimulators to apply a stimulus to the patient's body independently of any patient input, subsequently receives data representative of a perceived stimulus from the patient input interface, and subsequently provides the output with data representative of the applied stimulus for communication to the patient such that the data representative of the applied stimulus identifies, or allows the identification of, the applied stimulus.

DETAILED DESCRIPTION

In particular, as the controller provides the output with data representative of the applied stimulus for communication to the patient, such that the data representative of the applied stimulus identifies, or allows the identification of, the applied stimulus, subsequent to the controller receiving data representative of a perceived stimulus from the patient input interface, the patient stimulation device of the present invention may allow for feedback of the applied stimulus to a patient, such that a patient can learn the effect (eg feeling) of the applied stimulus on their body.

Thus the device may allow for device-led sensory discrimination training of a patient, thereby removing the need for the presence of a third party, for example a doctor or a nurse, to provide such sensory discrimination training manually. The patient stimulation device may thereby reduce the cost associated with sensory discrimination training, and may free-up time for doctors and nurses to perform other tasks, such that hospital or clinic efficiency is improved. The patient stimulation device may also be more convenient for the patient as the sensory discrimination training may be applied at a place and time which suits the patient. This may lead to better patient adherence to the treatment prescribed by a clinician.

The device according to the present invention may thereby enhance a user's body perception or body image, of a body part. The device may be used with any patient that requires an enhanced perception of a body part. For example the device may be used with the following types of patient: individuals with a painful body part; individuals who have undergone an impairment to their nervous system (for example stroke victims); individuals with impaired body image (for example those with eating disorders); individuals with chronic musculoskeletal conditions/injuries such as chronic ankle stability; and individuals who may wish to enhance their body image beyond the norm such as sports persons.

The data representative of the applied stimulus may be data representative of the position and/or duration and/or form of the applied stimulus. The form of the stimulus may be a continuous stimulus, a periodic stimulus, or an intermittent stimulus. For example, a periodic stimulus may comprise a plurality of individual stimuli applied at a constant rate, whilst an intermittent stimulus may comprise a plurality of individual stimuli applied at a varying rate.

The data representative of a perceived stimulus may be representative of a perceived stimulus location and/or a perceived stimulus duration.

The data representative of the applied stimulus may additionally comprise an indication as to whether the perceived stimulus matches the applied stimulus. For example, the device may communicate to a patient whether or not their perceived stimulus matches the applied stimulus. Where the perceived stimulus does not match the applied stimulus, the device may communicate the correct applied stimulus to a patient. The device may communicate to a patient the correct position and/or intensity and/or form of the applied stimulus. The device may repeat the applied stimulus where the perceived stimulus does not match the applied stimulus. Thus the device may allow a patient to learn the correct form of an applied stimulus where the applied stimulus is not recognised.

The controller may actuate at least one of the plurality of stimulators to apply a stimulus to the patient's body independently of any patient input. The controller may actuate a subsequent one of the plurality of stimulators to apply a stimulus to the patient's body after data representative of a previous applied stimulus has been communicated to a patient. For example, the controller may automatically repeat the steps of actuation, patient input, and communication, with different applied stimuli. The controller may actuate stimulators for a pre-determined number of applied stimuli. The repeated stimulator actuations may comprise stimulator actuations of a different time and/or intensity and/or form.

The controller may have a training mode in which the controller actuates at least one of the plurality of stimulators to apply a stimulus to a pre-determined position on a patient's body, which may be independent of any patient input, subsequently receives data representative of a perceived stimulus position from the patient input interface, and subsequently provides the output with data representative of the applied stimulus position for communication to the patient.

The controller may have an automatic familiarisation mode, the automatic familiarisation mode comprising the controller:
(a) actuating at least one of the plurality of stimulators to apply a stimulus to a patient's body, and
(b) subsequently providing the output with data representative of the applied stimulus for communication to the patient.

This mode of the device may be beneficial as it may allow a patient to familiarise themselves with a pre-determined applied stimulus.

The automatic familiarisation mode may comprise the controller actuating at least one of the plurality of stimulators to apply a stimulus to a pre-determined position on a patient's body, and/or at a pre-determined intensity, and/or in a pre-determined form. The automatic familiarisation mode may comprise providing the output with data representative of a pre-determined position and/or pre-determined intensity and/or pre-determined form of an applied stimulus for communication to the patient.

The controller may have a manual familiarisation mode, the manual familiarisation mode comprising the controller actuating at least one of the plurality of stimulators to apply a stimulus to the patient's body in response to patient input via the patient input interface. For example, the stimulus position, and/or the form and/or intensity of the applied stimulus, may be chosen by a patient using the patient interface.

This mode of the device may be beneficial as it may allow a patient to familiarise themselves with an applied stimulus of their choosing.

The controller may have an assessment mode, the assessment mode comprising the controller:
(a) actuating at least one of the plurality of stimulators to apply a stimulus to the patient's body, which we may be independent of any patient input,
(b) subsequently receiving data representative of a perceived stimulus from the patient input interface, and
(c) subsequently providing the output with data representative of the applied stimulus for communication to the patient, such that the data representative of the applied stimulus identifies, or allows the identification of, the applied stimulus.

In the assessment mode, the controller may actuate the plurality of stimulators to apply stimuli to a patient's body in a random sequence. The controller may receive data representative of a perceived stimulus from the patient input interface after each applied stimulus, and the controller may provide the output with data representative of the number of times the perceived stimulus matched the applied stimulus once the random sequence has finished.

By a random sequence it is meant a sequence which appears random to a patient, but which is a pre-determined sequence programmed into the controller.

The assessment mode may be beneficial as it may allow a patient to test their recognition of a random sequence of device stimulator actuations.

The training mode and/or assessment mode may comprise a user, for example a patient or healthcare professional, selecting a difficulty level of operation. The difficult level may be independently selected for different body parts or locations on the body, such that the treatment may be specific to a particular body part or location on the body. The training mode and/or assessment mode may comprise the controller actuating the stimulators in a random sequence based on the user-selected difficulty level.

The training and/or assessment mode may comprise a pre-programmed treatment path, which comprises pre-determined training and assessment stages. The pre-determined training and assessment stages of a treatment path may be made available as the patient successfully completes an assessment stage, for example obtaining at least a pre-determined threshold score.

In different difficulty levels, the controller may actuate different sets of stimulators of the device, eg sets of stimulators with different separations between immediately adjacent stimulators. For example, the controller may actuate in an easier level a set of stimulators that are located further apart from each other than a set of stimulators actuated in a more difficult level, and in a more difficult level the controller may actuate a set of stimulators that are located closer together than in an easier difficulty level. The controller may therefore actuate a smaller sub-set of the stimulators in an easier level relative to the set of stimulators actuated in a more difficult level.

The controller may, for example, comprise a microprocessor or microchip, or may, for example, be a separate component.

The patient stimulation device may store data and/or may transfer data to a storage system. The patient stimulation device may store data representative of applied stimuli, and may, for example, store the position and/or duration and/or form, of applied stimuli. In particular, the patient stimulation device may store pre-programmed treatment paths, which comprise pre-determined training and assessment stages. These pre-programmed treatment paths may be supplied with the device. Alternatively, or in addition, the device may enable a healthcare professional to program custom training and/or assessment modes, and in particular the particular stimulator actuations to be applied.

The storage system may comprise a local memory unit, or virtual storage, for example cloud storage. In particular, the patient stimulation device may download software, which contains a pre-programmed training mode and/or assessment mode, or indeed any other mode, or may even be controlled by software running on a remote device or in the cloud, for example.

The patient stimulation device may also store data representative of perceived stimuli, and may, for example, store the position and/or duration and/or form, of perceived stimuli.

The patient stimulation device may store or transfer data indicative of the number of times a perceived stimulus matches an applied stimulus. The device may also store or transfer data indicative of how often the device has been used. The patient stimulation device may transfer data indicative of the number of times a perceived stimulus matches an applied stimulus and/or the number of times the device has been used to a clinician, for example remotely via Bluetooth® or the like.

The controller may compare stored data to data received via the patient input interface. The controller may compare data representative of a perceived stimulus to data representative of an applied stimulus, for example, data representative of an applied stimulus stored by the patient stimulation device.

The controller may communicate data representative of an applied stimulus via a display unit. The data representative of the applied stimulus that is communicated to a patient may be determined by a comparison between stored data and data received via the patient input interface. The data representative of the applied stimulus that is communicated to a patient may be determined by a comparison between data representative of a perceived stimulus to data representative of an applied stimulus, for example, data representative of an applied stimulus stored by the patient stimulation device.

The patient stimulation device may comprise a housing for housing electronic components, including, for example, a microprocessor and associated circuitry. The housing may be shaped and dimensioned such that the device comprises a handheld device, for example a device which can be held in the hand of a user during use.

The patient stimulation device may be attachable to a display unit, for example a display screen, and/or may be attachable to an input device, for example a keyboard or a touchscreen or the like.

The plurality of stimulators may apply a stimulus to a patient's body in response to an initiation signal from the device. Only one of the plurality of stimulators may apply a stimulus to a patient's body in response to an initiation signal from the device. The initiation signal from the device may be determined by the mode of operation of the controller that is chosen by a patient.

The plurality of stimulators may apply a stimulus to a patient's body in response to an initiation signal applied to the device by a patient. Only one of the plurality of stimulators may apply a stimulus to a patient's body in response to an initiation signal applied to the device by a patient. The initiation signal applied to the device by a patient may correspond to the patient's selection of a mode of operation of the controller.

The plurality of stimulators may apply stimuli of different forms, for example stimuli of different intensities or durations. The plurality of stimulators may apply a continuous stimulus to a patient's body, for example an uninterrupted stimulus, or may apply a discontinuous stimulus to a patient's body, for example an interrupted stimulus in the form of a plurality of bursts.

The plurality of stimulators may apply stimuli of at least 1 mA, at least 5 mA, at least 10 mA, at least 25 mA, at least 50 Ma, or at least 75 mA. The plurality of stimulators may apply stimuli lasting at least 0.1, or 0.2, or 0.5, or 1, or 2, or 3, or 4, or 5 second(s). The plurality of stimulators may apply stimuli having a frequency of at least 2 Hz, at least 5 Hz, at least 10 Hz, at least 25 Hz, at least 50 Hz, or at least 150 Hz.

In different difficulty levels, the controller may apply different intensities of stimuli and/or the controller may apply different durations, eg pulse durations, of stimuli. The controller may apply, in an easier level, stimuli having a greater intensity and/or greater duration than the stimuli applied in a more difficult level. For example, in an easy level of operation, the controller may apply stimuli of at least 75 mA and/or the controller may apply stimuli lasting at least 4 seconds. In a difficult level of operation, the controller may apply stimuli of between 1 mA and 10 mA and/or the controller may apply stimuli lasting 0.1 seconds to 0.5 seconds. In an intermediate level of operation, the controller may apply stimuli of between 10 mA and 50 mA and/or the controller may apply stimuli lasting between 1 and 3 seconds.

The plurality of stimulators may be connected to the device by wires, or may be wirelessly connected to the device. The wires may be at most 50 cm, at most 75 cm, or at most 100 cm, long.

The plurality of stimulators may be attachable to a patient's body, and may, for example, be attachable to a patient's body via use of an adhesive or the like. The plurality of stimulators may comprise adhesive, and may, for example, comprise self-adhesive pads.

The plurality of stimulators may be locatable in different positions upon a patient's body, and may, for example, be locatable in any of the following regions: forearm; upper arm; elbow; shoulder; wrist; ankle; knee; thigh; or back.

The modes of the controller may comprise different settings corresponding to different treatment paths, for example different methods of treatment. Different locations upon the body may require different treatment paths. Treatment paths may comprise, for example, different durations and/or forms and/or positions of stimulations applied to the body. Treatment paths may increase and/or decrease in difficulty corresponding to a patient's needs.

Settings of the modes of the controller may be preconfigured by a clinician prior to use of the device by a patient, and may, for example, be configured remotely via use of software such as an app, or cloud based software.

The patient stimulation device may therefore enable a user to select the particular body position before each use, which may then select the appropriate treatment path for that body position. Furthermore, the controller may store data regarding the stage in a treatment path, for a particular body position, that the user has reached. This data may then enable the device to present the particular stage reached on a subsequent use of the device.

Each of the plurality of stimulators may be locatable in a different position upon a patient's body, such that no two stimulators share the same position upon a patient's body. The plurality of stimulators may be locatable in a regular array upon a patient's body, for example in a grid-like pattern. The distance and/or spacing between each of the plurality of stimulators may be variable, and may, for example, be altered by a patient. The distance and/or spacing between each of the plurality of stimulators may be altered by a patient to increase and/or decrease the difficulty of correctly identifying the position of an applied stimulus.

The distance between each of the plurality of stimulators may be at least 5%, at least 6%, at least 7%, at least 8%, at least 9%, or at least 10%, more than the patient's 2-point discrimination threshold, and, for example, the distance between any two of the plurality of stimulators may be at least 5%, at least 6%, at least 7%, at least 8%, at least 9%, or at least 10%, more than the patient's 2-point discrimination threshold. The patient's 2-point discrimination threshold may be the minimum distance between two points on the skin that can be detected by the patient.

The position of the plurality of stimulators may be altered by a patient to increase and/or decrease a difficulty level associated with use of the device. The position of the plurality of stimulators may be altered by a patient to increase and/or decrease the difficulty of correctly identifying the position of an applied stimulus. The position of the plurality of stimulators may be moved closer together to increase the difficulty of correctly identifying the position of an applied stimulus. The position of the plurality of stimulators may be altered by moving the stimulators or by actuating a set of stimulators that are closer together than another set of stimulators, within the same device.

The plurality of stimulators may apply an electrical stimulus to a patient's body, and may, for example, comprise electrical stimulators. The plurality of stimulators may comprise electrodes, and, for example, each of the plurality of stimulators may comprise a pair of electrodes.

The pair of electrodes may comprise one electrode configured to apply an electrical stimulus to a patient's body, and one electrode configured to remove an electrical stimulus from a patient's body. The pair of electrodes may comprise a cathode and an anode.

Where each pair of electrodes comprises a cathode and an anode, the position of first and second pairs of electrodes may be altered by a patient to increase and/or decrease a difficulty level associated with use of the device. For example, a first pair of electrodes may be brought closer to a second pair of electrodes to increase the difficulty level associated with use of the device and/or a first pair of electrodes may be moved away from a second pair of electrodes to decrease the difficulty level associated with use of the device. The position of first and second pairs of electrodes may be altered by a patient to increase and/or decrease the difficulty of correctly identifying the position of an applied stimulus.

The patient input interface may comprise a patient input interface for inputting data representative of a perceived position and/or intensity and/or form of an applied stimulus upon a patient's body. The perceived position and/or perceived intensity and/or perceived form of the applied stimulus may correspond to a perceived actuation of a stimulator by the device.

The patient input interface may be receive audio, and may be speech activated, eg utilising speech recognition. The controller of the patient stimulation device may be configured to be operable in response to a patient's voice. For example, a user may set the mode of operation of the patient stimulation device using their voice, and/or may provide data representative of a perceived stimulus using their voice.

The patient input interface may be gesture activated. The controller of the patient stimulation device may be configured to be operable in response to a gesture made by a patient. For example, a user may set the mode of operation of the patient stimulation device using a gesture, and/or may provide data representative of a perceived stimulus using a gesture. The patient input interface may comprise a sensor for sensing a gesture made by a patient.

The patient input interface may be activated by brain electrical activity of a patient. The controller of the patient stimulation device may be configured to be operable in response to brain electrical activity of a patient.

The patient input interface may comprise at least one button, and may, for example, comprise a plurality of buttons. At least one of the plurality of buttons may correspond to a stimulator, and may, for example correspond to a single stimulator. Thus, where a patient perceives a stimulator actuation, the patient may be able to use the plurality of buttons to indicate which stimulator they believe has been actuated by the device.

The at least one button may comprise a sensory feedback button, for example, a button which provides sensory feedback to a user in the form of a click when the button is depressed. The at least one button may comprise a capacitive sensing button, for example, a button in the form of an icon on a touchscreen device.

The patient input interface may comprise a touchscreen interface.

The patient input interface may be configured to allow a patient to choose a mode of operation of the device. For example, the patient input interface may comprise a plurality of buttons which allows the mode of operation of the device to be chosen by a patient. The patient input interface may be configured to allow a patient to select a body part to be treated, and hence which pre-configured treatment path the controller operates.

The output may comprise a display unit. The display unit may comprise a screen, and may, for example, comprise a touchscreen. The display unit may be configured to indicate a stimulator actuation, in use, and may, for example, be configured to indicate a stimulator actuation in response to patient input using the patient input interface.

The display unit may comprise a plurality of zones, and each of the plurality of zones may correspond to a stimulator, for example a single stimulator. The plurality of zones may provide visual indicia to a patient, the visual indicia being representative of an actuation of a stimulator. The plurality of zones may, for example be illuminated, or change colour, to represent actuation of a stimulator, and may, for example, be illuminated, or change colour, in response to data inputted by a user.

The display unit may comprise a display unit for displaying data representative of the position and/or intensity and/or form of an applied stimulus upon a patient's body.

The display unit may display data representative of the device stimulator actuation directly in response to data inputted by the patient. For example, the display unit may display data representative of the device stimulator actuation within at most 1 second, at most 2 seconds, at most 3 seconds, at most four seconds, or at most 5 seconds, of data input by a patient.

The patient stimulation device may output a signal representative of whether a perceived stimulus matches an applied stimulus, and may, for example, output an audible signal representative of whether a perceived stimulus matches an applied stimulus.

According to a fourth aspect of the invention there is provided a patient stimulation device comprising a plurality of stimulators for selectively applying a stimulus to a patient's body, the plurality of stimulators being provided on a band that fits around a body part of patient in use.

The band may be generally annular in form, when fitted. The band may comprise a resiliently deformable material, eg an elastic material. This material may allow the band to stretch or contract. The band may stretch or contract in a radial direction, in order that the circumference of the band may increase or decrease. The patient stimulation device may therefore be calibrated appropriately depending on the distance between the stimulators when fitted.

The advantage of providing a patient stimulation device wherein the electrodes are on a band that fits around a patient's body part is that the band is easy to wear and maintain in a desired position, with good contact between the stimulators and the skin of the patient.

The body part of a patient around which the band is fitted may be any of an arm, shoulder, wrist, ankle or thigh. There may be provided a range of patient stimulation devices of different sizes, wherein each stimulation device is sized to fit around a different body part.

The plurality of stimulators may be electrodes. The electrodes may be provided around the circumference of the band, in an electrode ring. The electrodes may be regularly spaced around the circumference of the band.

The band may be generally tubular in shape. The band may comprise a single electrode ring. Alternatively, there may be provided more than one electrode ring, eg two electrode rings. A first and second electrode ring may be separated along a length of the band. The distance between the first and second electrode ring may be adjustable. The material of the band may therefore stretch in a longitudinal direction.

The plurality of electrodes may be provided in a two-dimensional array across the band. The two-dimensional array may be a regular or irregular array.

The band may comprise a mesh or track wherein a user may arrange the electrodes in a desired array on the band. For example, a user may choose to locate the electrodes such that they are located close together, or alternatively the user may choose to arrange the electrodes such that they are located at larger distances from each other.

The patient stimulation device may comprise a patient input interface for receiving data representative of a perceived stimulus from the patient. The patient stimulation device may comprise an output for communicating to a patient data representative of an applied stimulus. The patient input interface and the output may comprise any of the features as hereinbefore described.

The stimulators may be connected to the patient stimulation device be a series of wires. The series of wires may be a bundle of wires, such that the band may be connected to the patient stimulation device by a cable.

The patient stimulation device may comprise a controller. The controller may have a training mode, as hereinbefore described in relation to the first, second and third aspects of the invention.

Preferential features of any of the aspects of the present invention may be applied to other aspects of the present invention, where appropriate.

BRIEF DESCRIPTION OF THE DRAWINGS

Practicable embodiments of the invention will now be described, with reference to the accompanying drawings, of which.

DETAILED DESCRIPTION

Figure 1:
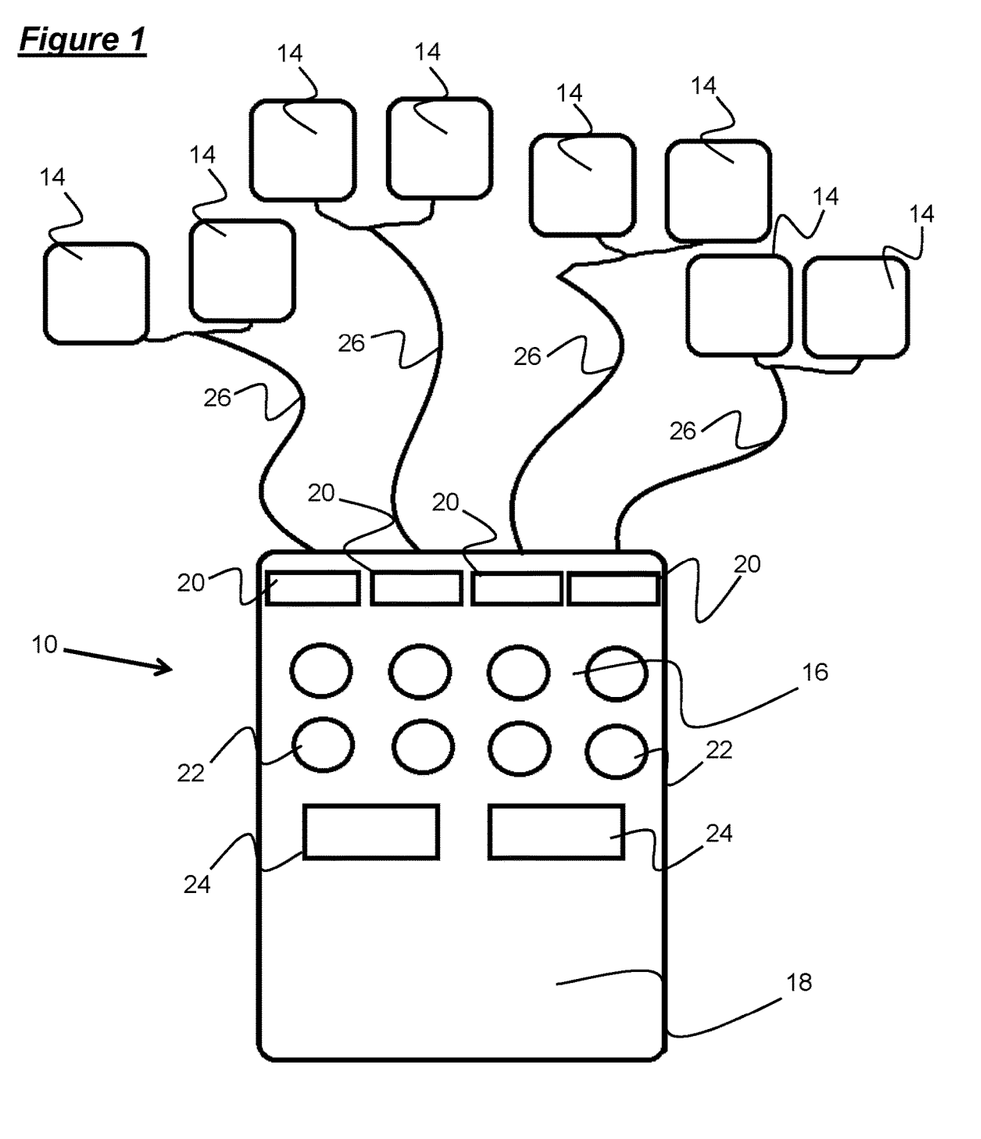
FIG. 1 is a schematic view of a first example of a device according to the present invention.
Figure 2:
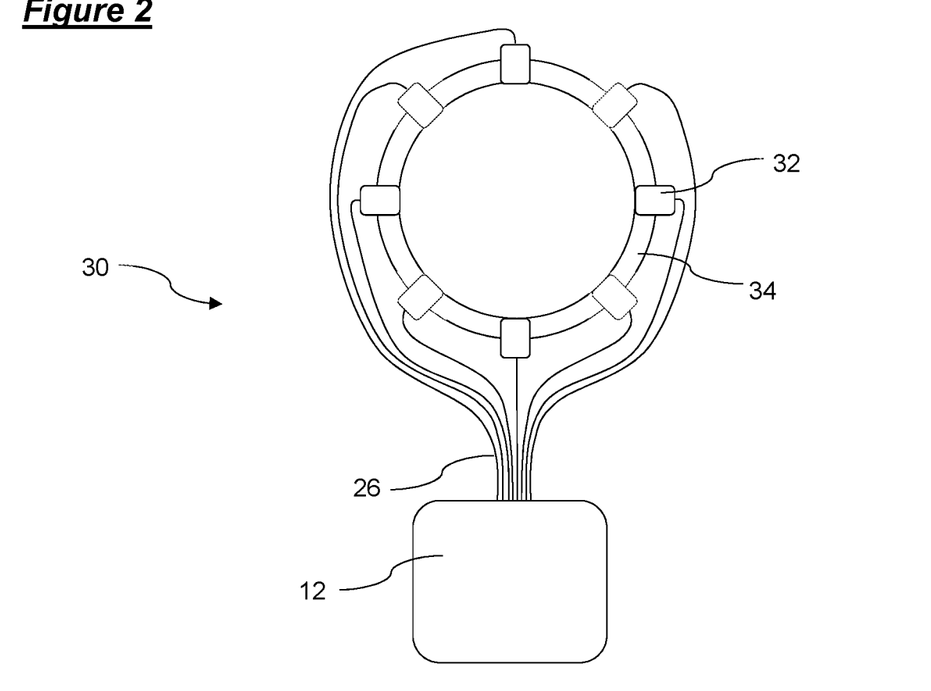
FIG. 2 is a schematic view of a second example of a device.
Figure 3:
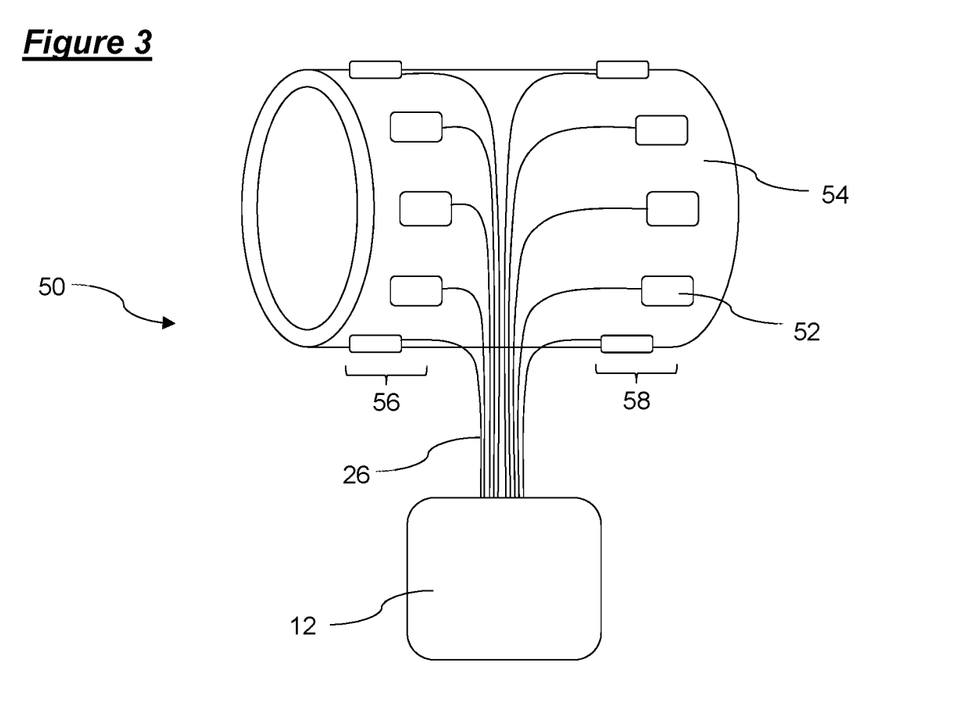
FIG. 3 is a schematic view of a third example of a device.

Four different examples of patient stimulation devices 10,30,50 are shown schematically in FIGS. 1 to 3. Each patient stimulation device 10,30,50 comprises the same combined patient input interface and display 12, and each patient stimulation device 10,30,50 comprises a plurality of electrodes.

As shown in detail in FIG. 1, the combined patient input interface and display 12 is a touchscreen device, similar in overall form to a mobile phone, or a tablet computer or the like. An upper surface of the combined patient input interface and display 12 is split into a patient input region 16 and a display region 18. The patient input region 16 occupies an upper half of the upper surface of the combined patient input interface and display 12, and comprises a plurality of mode selection icons 20, a plurality of stimulator icons 22, and a plurality of stimulus form icons 24. Each of the icons 20,22,24 is a touchscreen icon which functions as a capacitive sensing button.

The mode selection icons 20 are usable to select a mode of operation of the patient stimulation device 10. Each of the stimulator icons 22 corresponds to an electrode, and can be used to actuate an electrode, or to indicate which electrode a patient believes has been used to apply a stimulus, or to indicate to a patient which electrode has been used to apply a stimulus. Each of the stimulator form icons 24 can be used to choose the form of an applied stimulus, or to indicate which form of an applied stimulus a patient believes has been applied by an electrode, or to indicate to a patient the form of stimulus that has been applied by an electrode.

The display region 18 occupies a lower half of the upper surface of the combined patient input interface and display 12, and comprises a visual display screen.

The electrodes are attached to the patient stimulation device 10 by wires 26.

The patient stimulation device 10,30,50 also comprises a power button (not shown) for turning the device 10,30,50 on and off, and a settings button (not shown) for allowing the settings of the device to be changed.

FIG. 1 shows a first example of a patient stimulation device 10, comprising four pair of electrodes 14 and the patient input interface and display 12. The electrodes 14 are arranged in pairs, with one electrode 14 in a pair being a cathode, and the other electrode 14 in a pair being an anode. The electrodes 14 comprise self-adhesive pads which are capable of adhesion to human skin.

In use, a region of a patient's body is divided into four adjacent, spatially separated regions, in a grid-like manner. The distance between any two of the four regions is approximately 10% greater than the patient's 2-point discrimination threshold (which is the minimum distance between two points on the skin that can be detected by the patient). A pair of electrodes 14 (one cathode and one anode) is attached to each region, such that each region can be electrically stimulated via the electrodes 14.

FIGS. 2 and 3 show examples of the patient stimulation device, wherein the electrodes are provided on bands which fit around a patient's limb.

FIG. 2 shows a patient stimulation device 30 comprising eight electrodes 32 that are provided on a circular band 34. The eight electrodes 32 are regularly spaced around the patient's limb. The circular band 34 is a flexible elasticated cloth which may fit around a patient's limb in use, such that the electrodes 32 are spaced around the patient's limb.

FIG. 3 shows a similar patient stimulation device 50, comprising sixteen electrodes 52 which are provided on a tubular band 54 of a sock-like material. The electrodes 52 are provided in two rings 56, 58 which are each spaced around the band 54. The distance between the first and second rings 56, 58 of electrodes 52 is adjustable, due to the elasticity of the sock-like material of the band 54. In use, the band 54 can be worn around the limb of a patient, with each ring 56, 58 of electrodes 52 encircling the patient's limb, and the two rings 56, 58 being separated along the length of the patient's limb.

The patient stimulation device 10,30,50 can then be operated in one of four modes, which will be discussed in more detail below.

Figure 4:
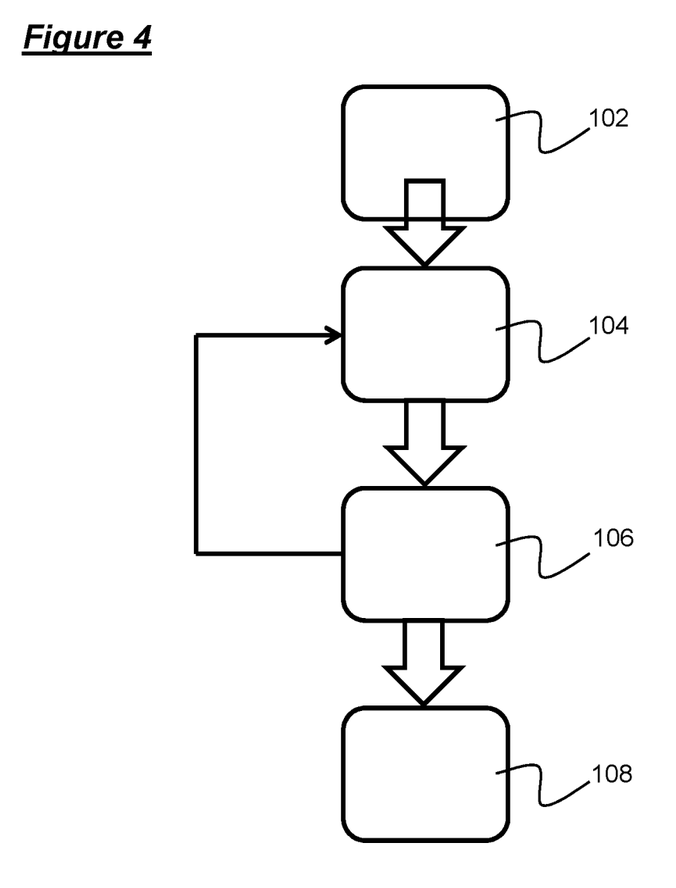
FIG. 4 is a flow diagram representative of a first mode of operation of the devices of FIGS. 1 to 3.

A flowchart schematically depicting a first mode of operation of the patient simulation device 10,30,50 is shown in FIG. 4. In the first mode of operation, a patient initially sets 102 the intensity of the stimulus to be applied by the electrodes 14,32,52. This is done via use of the icons 20,22,24. Once the intensity has been set, the intensity cannot be changed without turning off the device 10,30,50, such that the intensity cannot be accidentally increased by a patient during use. The patient may also then set the pulse rate, pulse duration, and on time of the single or burst stimulus to be applied, although these options will typically be pre-set.

Once the intensity has been set, the device 10,30,50 applies 104 a stimulus via one of the electrodes 32,52 or one of the pairs of electrodes 14. As the stimulus is being applied, the device 10,30,50 provides feedback 106 to the patient of the region to which the stimulus is being applied, and the form of the stimulus which is being applied, via the icons 20,22,24, and/or the display region. The device 10,30, 50 may also give auditory feedback via a speaker. Each of the electrodes 32,52 or pairs of electrodes 14 is stimulated in turn, in both a continuous mode and a burst (intermittent mode). The patient may then choose 108 to repeat this mode, or to move on to a different mode.

This mode of operation of the patient stimulation device 10,30,50 may thereby orientate the patient to which part of the body is being stimulated, the form of stimulation that is being applied, and what this stimulation feels like. Such a mode of operation may be referred to as an automatic familiarisation mode.

Figure 5:
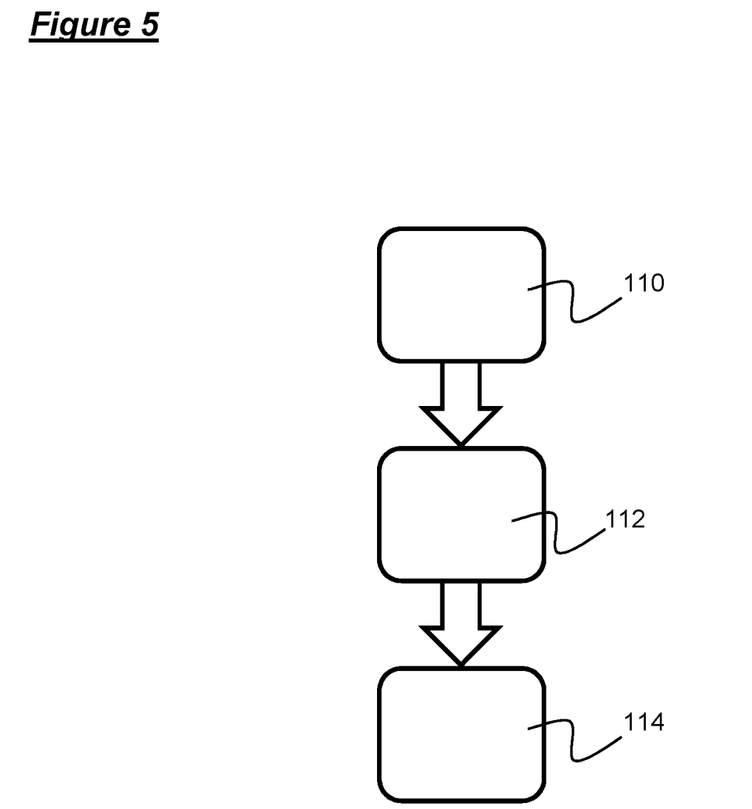
FIG. 5 is a flow diagram representative of a second mode of operation of the devices of FIGS. 1 to 3.

A flowchart schematically depicting a second mode of operation of the patient simulation device 10,30,50 is shown in FIG. 5. In the second mode of operation, a patient chooses the location of the stimulus to be applied 110, via use of the stimulator icons 22 to choose an electrode 32,52 or a pair of electrodes 14, and then chooses the form (ie continuous or burst) of the stimulus to be applied 112, via use of the stimulus form icons 24. The chosen stimulus is then applied 114 by the chosen pair of electrodes 14. This mode of operation may be exited by a patient at any given time.

This mode of operation of the patient stimulation device 10,30,50 may thereby allow a patient to manually orient themselves to a desired stimulus. Such a mode of operation may be referred to as a manual familiarisation mode.

Figure 6:
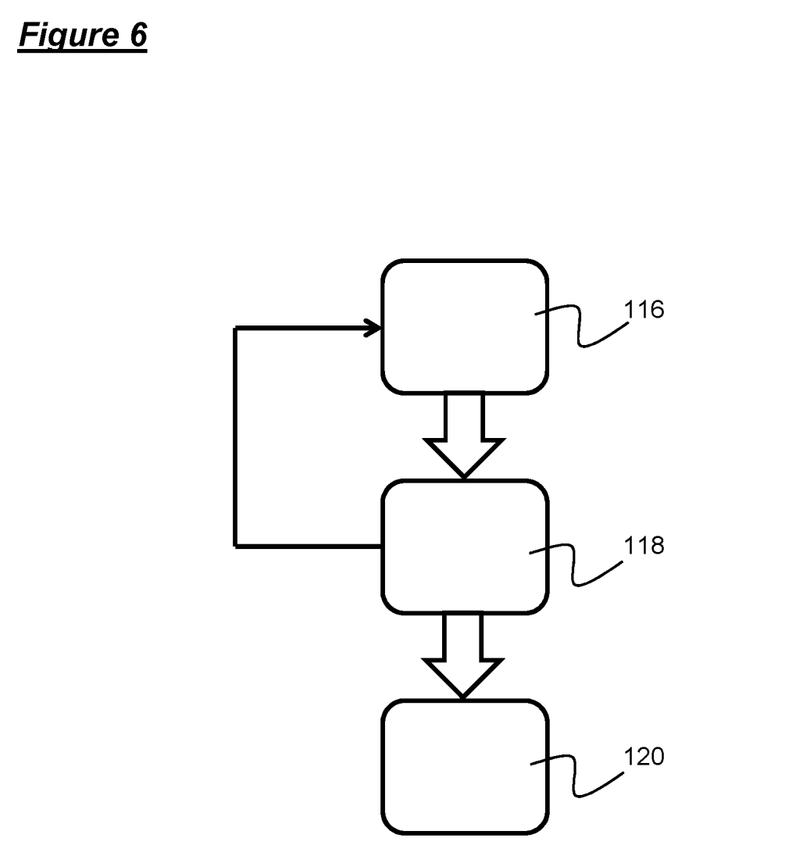
FIG. 6 is a flow diagram representative of a third mode of operation of the devices of FIGS. 1 to 3.

A flowchart schematically depicting a third mode of operation of the patient simulation device 10,30,50 is shown in FIG. 6. In the third mode of operation, each electrode 32,52 or pair of electrodes 14 is actuated 116 by the device 10,30,50 in a random order, and in a random form. After each actuation of an electrode 32,52 or pair of electrodes 14, the patient is invited to input 118, using the stimulator icons 22 and the stimulus form icons 24, the location and form of the stimulation that they perceived. Once a patient has inputted their choice, the next actuation of an electrode 32,52 or pair of electrodes 14 occurs. Once thirty stimuli have been applied, the display region 18 is used to present 120 an indication to the patient, in the form of a percentage score, of the number of times their perceived stimulation matched the stimulation that was actually applied by the device 10,30,50.

If a patient consistently obtains a score of over 90%, they may reduce the distance between the electrodes 14 of the device 10, or the distances between the rings 56,58 of the device 50, to increase the difficulty level of this mode.

If a score of 90% is not achieved, then the device 10,30,50 may suggest that the patient utilises the fourth mode of operation, which will be described in more detail below.

This third mode of operation of the patient stimulation device 10,30,50 may thereby test a patient's perception of the region in which the electrodes 14,32,52 are attached. Such a mode of operation may be referred to as an assessment mode.

Figure 7:
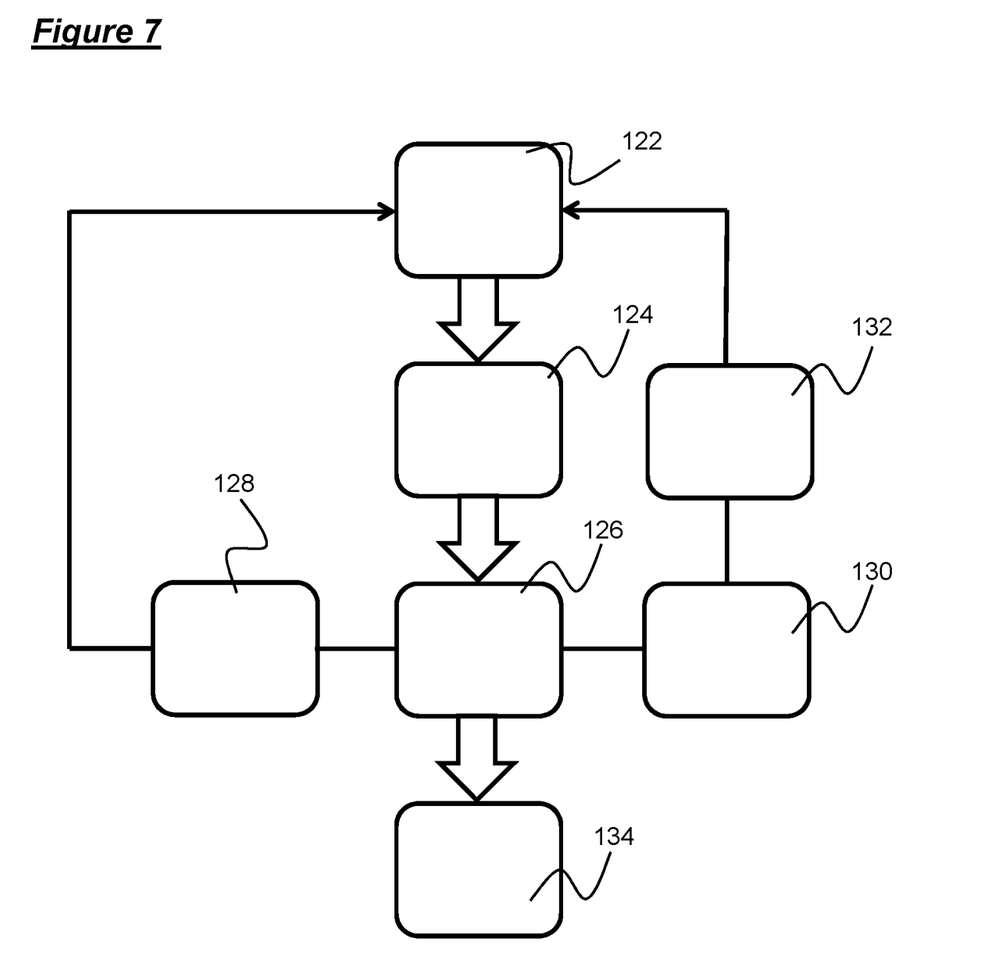
FIG. 7 is a flow diagram representative of a fourth mode of operation of the devices of FIGS. 1 to 3.

A flowchart schematically depicting a fourth mode of operation of the patient simulation device 10,30,50 is shown in FIG. 7. In the fourth mode of operation, each electrode 32,52 or pair of electrodes 14 is actuated 122 by the device 10,30,50 in a random order, and in a random form. After each actuation of an electrode 32,52 or pair of electrodes 14, the patient is invited to input 124, using the stimulator icons 22 and the stimulus form icons 24, the location and form of the stimulation that they perceived.

Once a patient has inputted their choice, the display region 18 is used to provide feedback 126 to the patient as to whether or not their perceived stimulation matches the stimulation that was actually applied by the device 10,30,50. If the perceived stimulation matches the applied stimulation, then the display region 18 provides a "CORRECT" reading 128, and the next actuation of an electrode 32,52 or pair of electrodes 14 occurs. If the perceived stimulation does not match the applied stimulation, then the display region 18 provides an "INCORRECT" reading 130. The icons 22,24 are used to indicate to a patient what the applied stimulus actually was, and the same stimulus is then applied 132 by the device 10,30,50, such that a patient knows the location and form of that stimulus. Once this has occurred, the next random actuation of an electrode 32,52 or pair of electrodes 14 occurs.

Once thirty stimuli have been applied, the display region 18 is used to present 134 an indication to the patient, in the form of a percentage score, of the number of times their perceived stimulation matched the stimulation that was actually applied by the device 10,30,50.

This mode of operation of the patient stimulation device 10,30,50 may thereby provide real time feedback to a patient as to whether their perception of the applied stimulus (and hence their body image) is correct. This mode may thereby be used to train a patient to enhance their perception of an applied stimulus, and hence enhance their mental body image, without the need for third party feedback in real time. Such a mode of operation may be referred to as a treatment or training mode.

Figure 8:
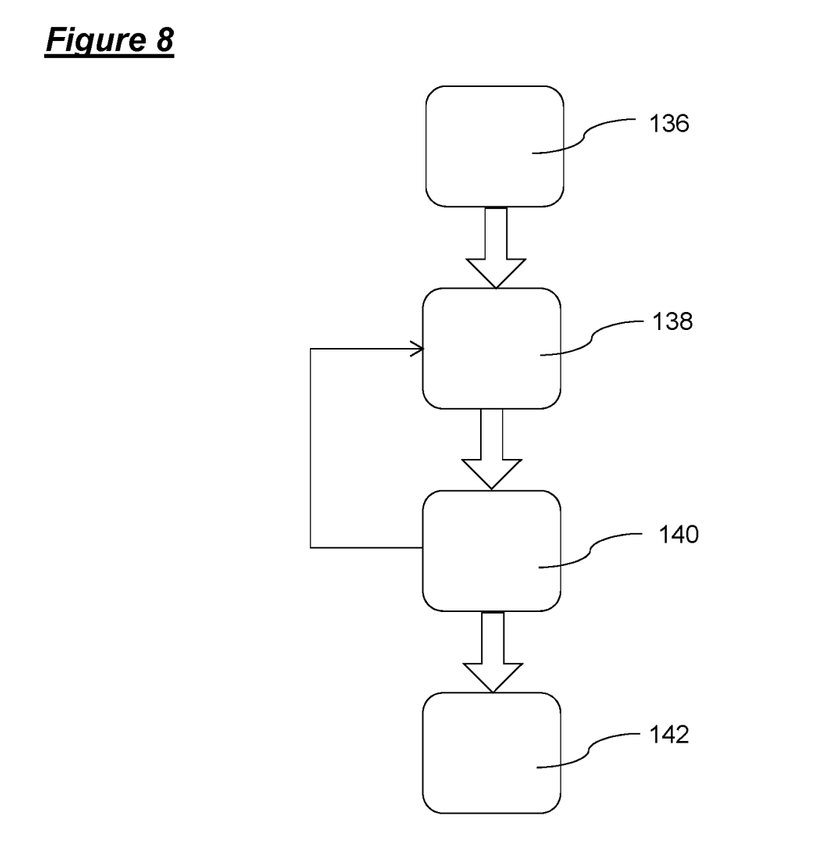
FIG. 8 is a flow diagram representative of a fifth mode of operation of the devices of FIGS. 1 to 3.

A flowchart schematically depicting a fifth mode of operation of the patient stimulation device 10,30,50 is shown in FIG. 8. In the fifth mode of operation, a user is asked 136 to select a difficulty level of operation. In an easy level, 4 electrodes 32,52 or 2 pairs of electrodes 14 are operable; in a moderate level, 6 electrodes 32,52 or 3 pairs of electrodes 14 are operable; and in a difficult level, 8 electrodes 32,52 or 4 pairs of electrodes 14 are operable. The desired number of electrodes 14,32,52 depending on the selected difficulty level, are actuated 138 by the device 10,30,50 in a random order, and in a random form. After each actuation of an electrode 32,52 or pair of electrodes 14 the patient is invited to input 140, using the stimulator icons 22 and the stimulus form icons 24, the location and form of the stimulation that they perceived. Once a patient has inputted their choice, the next actuation of an electrode 32,52 or pair of electrodes 14 occurs. Once thirty stimuli have been applied, the display region 18 is used to present 142 an indication to the patient, in the form of a percentage score, of the number of times their perceived stimulation matched the stimulation that was actually applied by the device 10,30,50.

If a patient consistently obtains a score of over 90%, they may change the difficulty level to a more difficult level. If a patient consistently obtains a score of less than 90%, they may wish to change the difficulty level to an easier level, or they may wish to instead use the fourth mode of operation.

This fifth mode of operation of the patient stimulation device 10,30,50 may test a patient's perception of the region in which the electrodes 14,32,52 are attached. Such a mode of operation may be referred to as an assessment mode.

In any of the third, fourth or fifth modes of operation of the patient stimulation device 10,30,50, the device 10,30,50 may record usage and/or the scores obtained by a patient, and this data may be sent remotely via Bluetooth®, or may be downloaded manually. This may allow a clinician to monitor a patient's compliance and progress in using the device 10,30,50, and may allow such compliance and progress to be monitored remotely.

What is claimed is:

1. A patient stimulation device comprising a plurality of stimulators configured to selectively apply a stimulus to a patient's body and a user interface having a plurality of inputs, the device having the same number of stimulators as inputs, the device having an input configuration in which each of the plurality of inputs is dedicated to a different stimulator and each stimulator is located on a different position of the body, wherein the user interface is configured to allow the patient to communicate to the device through the plurality of inputs of the user interface to indicate the patient's choice of at least position data representative of the location of the stimulator the patient believes has been actuated to apply a stimulus, and an output for communicating to the patient whether the patient's choice correctly identifies the location of the actuated stimulator, and if not at least position data representative of the location of the actuated stimulator that has been used to apply the stimulus, wherein the device comprises a controller having a training mode in which the controller is programmed to perform a stimulation cycle, the stimulation cycle comprising the steps of:

(a) actuating at least one of the plurality of stimulators to apply a stimulus to the patient's body, wherein the location of the actuated stimulator is unknown to the patient, (b) subsequently receiving communication from the patient through one of the plurality of inputs of the user interface indicating the patient's choice of at least position data representative of the location of the actuated stimulator the patient believes has been used to apply the stimulus, and (c) subsequently providing the output with data for communication to the patient, wherein the data provided to the output comprises whether the patient's choice correctly identifies at least the location of the actuated stimulator, and if not at least position data representative of the location of the actuated stimulator that has been used to apply the stimulus.

2. A patient stimulation device as claimed in claim 1, wherein the at least position data representative of the location of the stimulator that has been used to apply the stimulus is additionally representative of the intensity and/or form of the applied stimulus.

3. A patient stimulation device as claimed in claim 1, wherein the at least position data representative of the location of the stimulator the patient believes has been used to apply a stimulus is additionally representative of a perceived intensity and/or a perceived form of the applied stimulus.

4. A patient stimulation device as claimed in claim 1, wherein the controller is programmed to actuate a subsequent one of the plurality of stimulators after at least position data representative of the location of the stimulator that has previously been used to apply the stimulus is communicated to a patient.

5. A patient stimulation device as claimed in claim 1, wherein the patient stimulation device stores data, or transfers data to a storage system.

6. A patient stimulation device as claimed in claim 5, wherein the controller is programmed to compare stored data to at least position data representative of the location of the stimulator the patient believes has been used to apply a stimulus received via the user interface.

7. A patient stimulation device as claimed in claim 5, wherein the controller is programmed to compare at least position data representative of the location of the stimulator the patient believes has been used to apply a stimulus to at least position data representative of the location of the stimulator that has been used to apply the stimulus.

8. A patient stimulation device as claimed in claim 7, wherein the at least position data provided to the output is determined by a comparison between stored data and the at least position data representative of the location of the stimulator the patient believes has been used to apply a stimulus received via the user interface.

9. A patient stimulation device as claimed in claim 8, wherein the at least position data provided to the output is determined by a comparison between at least position data representative of the location of the stimulator the patient believes has been used to apply a stimulus to at least position data representative of the location of the stimulator that has been used to apply the stimulus.

10. A patient stimulation device as claimed in claim 1, wherein the patient stimulation device comprises a housing for housing electronic components, and the housing is shaped and dimensioned such that the device can be held in the hand of a user during use.

11. A patient stimulation device as claimed in claim 1, wherein the plurality of stimulators apply a stimulus to a patient's body in response to an initiation signal applied to the device by a patient.

12. A patient stimulation device as claimed in claim 1, wherein the user interface is speech or brain electrical activity or gesture activated.

13. A patient stimulation device as claimed in claim 1, wherein the device comprises a display unit, and the display unit comprises a screen.

14. A patient stimulation device as claimed in claim 1, wherein the controller has an automatic familiarisation mode in which the controller is programmed to:

(a) actuate at least one of the plurality of stimulators to apply a stimulus to a patient's body, and
(b) subsequently provide the output with data representative of the applied stimulus for communication to the patient.

15. A patient stimulation device as claimed in claim 1, wherein the controller has a manual familiarisation mode in which the controller is programmed to actuate at least one of the plurality of stimulators to apply a stimulus to the patient's body in response to patient input via the user interface.

16. A patient stimulation device as claimed in claim 1, wherein the controller has an assessment mode in which the controller is programmed to:

(a) actuate the plurality of stimulators to apply stimuli to a patient's body in a random sequence;
(b) receive communication from the patient through one of the plurality of inputs of the user interface indicating at least position data representative of the location of the stimulator the patient believes has been used to apply the stimulus after each applied stimulus; and
(c) subsequently provide the output with data for communication to the patient, wherein the patient stimulation device stores at least position data representative of the location of the stimulator that has been used to apply each stimulus, and the data provided to the output comprises at least data representative of the number of times the indication of the location of the stimulator the patient believes has been used to apply each stimulus matched the location of the stimulator that has been used to apply each stimulus stored by the patient stimulation device once the random sequence has finished.

17. A patient stimulation device as claimed in claim 1, wherein steps (a)-(c) of the stimulation cycle are repeated.

18. A method of applying a stimulus to a patient's body using a patient stimulation device, the device comprising a plurality of stimulators for selectively applying a stimulus to a patient's body and a user interface having a plurality of inputs, the device having the same number of stimulators as inputs, the device having an input configuration in which each of the plurality of inputs is dedicated to a different stimulator and each stimulator is located on a different position of the body, the user interface configured for receiving communication from the patient through the plurality of inputs of the user interface indicating the patient's choice of at least position data representative of the location of the stimulator the patient believes has been actuated to apply a stimulus, an output for communicating to the patient whether the patient's choice correctly identifies the location of the actuated stimulator, and if not at least position data representative of the location of the actuated stimulator that has been used to apply the stimulus, and a controller having a training mode for performing a stimulation cycle, the method comprising performing the stimulation cycle comprising the steps of:

(a) actuating at least one of the plurality of stimulators to apply a stimulus to the patient's body, wherein the location of the actuated stimulator is unknown to the patient,
(b) subsequently receiving communication from the patient through one of the plurality of inputs of the user interface indicating the patient's choice of at least position data representative of the location of the actuated stimulator the patient believes has been used to apply the stimulus, and (c) subsequently providing the output with data for communication to the patient, wherein the data provided to the output comprises whether the patient's choice correctly identifies at least the location of the actuated stimulator, and if not at least position data representative of the location of the actuated stimulator that has been used to apply the stimulus.

19. A data carrier comprising machine readable instructions for a controller of a patient stimulation device, the device comprising a plurality of stimulators for selectively applying a stimulus to a patient's body and a user interface having a plurality of inputs, the device having the same number of stimulators as inputs, the device having an input configuration in which each of the plurality of inputs is dedicated to a different stimulator and each stimulator is located on a different position of the body, the user interface configured for receiving communication from the patient through the plurality of inputs of the user interface indicating the patient's choice of at least position data representative of the location of the stimulator the patient believes has been actuated to apply a stimulus, an output for communicating to the patient whether the patient's choice correctly identifies the location of the actuated stimulator, and if not at least position data representative of the location of the actuated stimulator that has been used to apply the stimulus, and the controller having a training mode, wherein the instructions cause operation of the controller for performing a stimulation cycle to:
  (a) actuate at least one of the plurality of stimulators to apply a stimulus to the patient's body, wherein the location of the actuated stimulator is unknown to the patient,
  (b) subsequently receiving communication from the patient through one of the plurality of inputs of the user interface of indicating the patient's choice of at least position data representative of the location of the actuated stimulator the patient believes has been used to apply the stimulus, and
  (c) subsequently providing the output with data for communication to the patient, wherein the data provided to the output comprises whether the patient's choice correctly identifies at least the location of the actuated stimulator, and if not at least position data representative of the location of the actuated stimulator that has been used to apply the stimulus.

\* \* \* \* \*